(12) United States Patent
Darrow et al.

(10) Patent No.: US 8,885,904 B2
(45) Date of Patent: Nov. 11, 2014

(54) SYSTEMS AND METHODS FOR LANDMARK CORRECTION IN MAGNETIC RESONANCE IMAGING

(75) Inventors: Robert David Darrow, Scotia, NY (US); Thomas Foo, Clifton Park, NY (US); Maggie Fung, Waukesha, WI (US); Vivek Prabhakar Vaidya, Bangalore (IN); Xiaodong Tao, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 280 days.

(21) Appl. No.: 13/451,228

(22) Filed: Apr. 19, 2012

(65) Prior Publication Data

US 2013/0279779 A1 Oct. 24, 2013

(51) Int. Cl.
*G06K 9/00* (2006.01)
(52) U.S. Cl.
USPC .......................................... 382/131; 382/128
(58) Field of Classification Search
USPC .................................. 382/128, 131
See application file for complete search history.

(56) References Cited

U.S. PATENT DOCUMENTS

| | | | | |
|---|---|---|---|---|
| 6,410,919 | B1* | 6/2002 | Nickles | 250/363.03 |
| 7,204,254 | B2 | 4/2007 | Riaziat et al. | |
| 7,450,983 | B2 | 11/2008 | Weiss | |
| 7,715,607 | B2 | 5/2010 | Hu et al. | |
| 2004/0105574 | A1* | 6/2004 | Pfaff | 382/128 |
| 2006/0078195 | A1* | 4/2006 | Vaillant et al. | 382/154 |
| 2009/0067696 | A1 | 3/2009 | Bystrov et al. | |
| 2009/0123111 | A1* | 5/2009 | Udd | 385/13 |
| 2010/0004527 | A1* | 1/2010 | Dale et al. | 600/410 |
| 2010/0067764 | A1 | 3/2010 | Lu et al. | |
| 2010/0125285 | A1* | 5/2010 | Sewell et al. | 606/130 |
| 2011/0211744 | A1 | 9/2011 | Darrow et al. | |
| 2012/0019246 | A1* | 1/2012 | Kannengiesser et al. | 324/309 |

FOREIGN PATENT DOCUMENTS

SG 155252 A1 9/2009

OTHER PUBLICATIONS

Julien.,"Model-based Intensity Nonuniformity Correction in Brain MRI", 7th International Conference on Signal Processing Proceedings, vol. 2, pp. 982-985, Aug. 31-Sep. 4, 2004.
Xue.,"Automatic Segmentation and Reconstruction of the Cortex from Neonatal MRI", NeuroImage, vol. 38, Issue 3, pp. 461-477, Nov. 15, 2007.
Zhang.,"Automated Alignment of MRI Brain Scan by Anatomic Landmarks", Proc. of SPIE—Medical Imaging: Image Processing, vol. 7259, Mar. 27, 2009.
Liu et al.,"Landmark Optimization Using Local Curvature for Point-Based Nonlinear Rodent Brain Image Registration", International Journal of Biomedical Imaging, vol. 2012, 2011.

* cited by examiner

*Primary Examiner* — Gregory F Cunningham
(74) *Attorney, Agent, or Firm* — Melissa K. Dobson

(57) ABSTRACT

Systems and methods for landmark correction in Magnetic Resonance Imaging (MRI) are provided. One method includes acquiring at least one calibration image or at least one localizer image of an object, identifying in the calibration or localizer images a region of the object as a reference point, wherein the reference point defines a landmark position. The method further includes determining an offset between an initial landmark position and the identified landmark position. The method also includes using the determined offset for MRI.

27 Claims, 12 Drawing Sheets

SYSTEMS AND METHODS FOR LANDMARK CORRECTION IN MAGNETIC RESONANCE IMAGING

BACKGROUND

Diagnostic imaging procedures often use specific scan configurations that allow acquisition and reconstruction of imaging data from a desired region of interest (ROI) of a subject, such as a patient. Magnetic Resonance Imaging (MRI), for example, includes a plurality of scan configurations that specify parameters related to patient position, positioning of radio-frequency coils (RF) and landmarking an ROI of the patient for specific imaging protocols. In particular, landmarking registers a patient with a scanner coordinate system to allow an imaging volume to be moved to a homogeneous, imaging portion, for example, an iso-center of a magnet of the MRI system for desired imaging.

The landmarking process is many times a manual process in which a MRI system operator defines the center of an imaging region through mechanical, optical, or other suitable means. For example, the system operator may position the patient on an examination table, position a magnet resonance (MR) coil at a desired ROI of the patient, followed by manually positioning the table within the magnet bore such that the desired ROI coincides with scanner alignment mechanisms (e.g., alignment lights). The quality and consistency of landmarking and patient positioning in these arrangements, thus, mostly relies on the operator's skill and experience.

Thus, in many conventional MRI exams, the patient is manually landmarked by the scanner operator at the beginning of the exam. The landmark procedure, like any human process, is subject to error. While a landmark error is undesirable, it is also problematic in the context of a MRI examination with automated scan plane prescription. If the patient is improperly landmarked by the operator, images used for the automated scan plane prescription may not contain the patient anatomy needed for proper computation of scan planes. Consistency in manual landmarking, however, may be difficult for complex anatomies like the heart or joints, sometimes leading to incorrect patient positioning. In particular, an error in judging the relative position of the coil by the operator may cause the center of the coil to be positioned at an offset from the iso-center to a less homogenous position of the magnet.

Thus, a patient landmark may be incorrectly placed by the scanner operator, causing one or more problems when scanning or resulting in the acquisition of images of sub-par image quality. Additionally, natural or pathology driven variations in patient anatomy can make the problem of finding a correct localizer visually challenging. Accordingly, because clinical decisions regarding diagnosis and treatment of disease conditions are often made based on certain image-derived parameters, accurate characterization of specific features of the anatomy of interest allows for a better understanding of patient anatomy and physiology, which in turn aids in diagnosis. Inaccurate estimations of clinically relevant parameters such as a location of a lesion derived from images reconstructed using erroneous configurations, thus, may lead to incorrect diagnosis. This is especially the case in follow-up examinations where morphological changes between examinations are used to assess the efficacy of a treatment or progression of disease.

BRIEF DESCRIPTION

In accordance with various embodiments, a method for landmark correction in Magnetic Resonance Imaging (MRI) is provided. The method includes acquiring at least one calibration image or at least one localizer image of an object, and identifying in the calibration or localizer images a region of the object as a reference point, wherein the reference point defines a landmark position. The method further includes determining an offset between an initial landmark position and the identified landmark position. The method also includes using the determined offset for MRI.

In accordance with other various embodiments, a non-transitory computer readable storage medium for landmark correction in Magnetic Resonance Imaging (MRI) using a processor is provided. The non-transitory computer readable storage medium includes instructions to command the processor to acquire at least one calibration image or at least one localizer image of an object and identify in the calibration or localizer images a region of the object as a reference point, wherein the reference point defines a landmark position. The non-transitory computer readable storage medium further includes instructions to command the processor to determine an offset between an initial landmark position and the identified landmark position. The computer readable storage medium also includes instructions to further command the processor to use the determined offset for MRI.

In accordance with yet other various embodiments, a Magnetic Resonance Imaging (MRI) system is provided that includes an imaging portion configured to acquire MRI images including at least one calibration image or localizer image of an object. The MRI system also includes a processing portion having a landmark correction module configured to identify in the calibration or localizer images a region of the object as a reference point, wherein the reference point defines a landmark position. The landmark correction module is further configured to determine an offset between an initial landmark position and the identified landmark position and use the determined offset for MRI imaging by the imaging portion.

DETAILED DESCRIPTION

Figure 1:
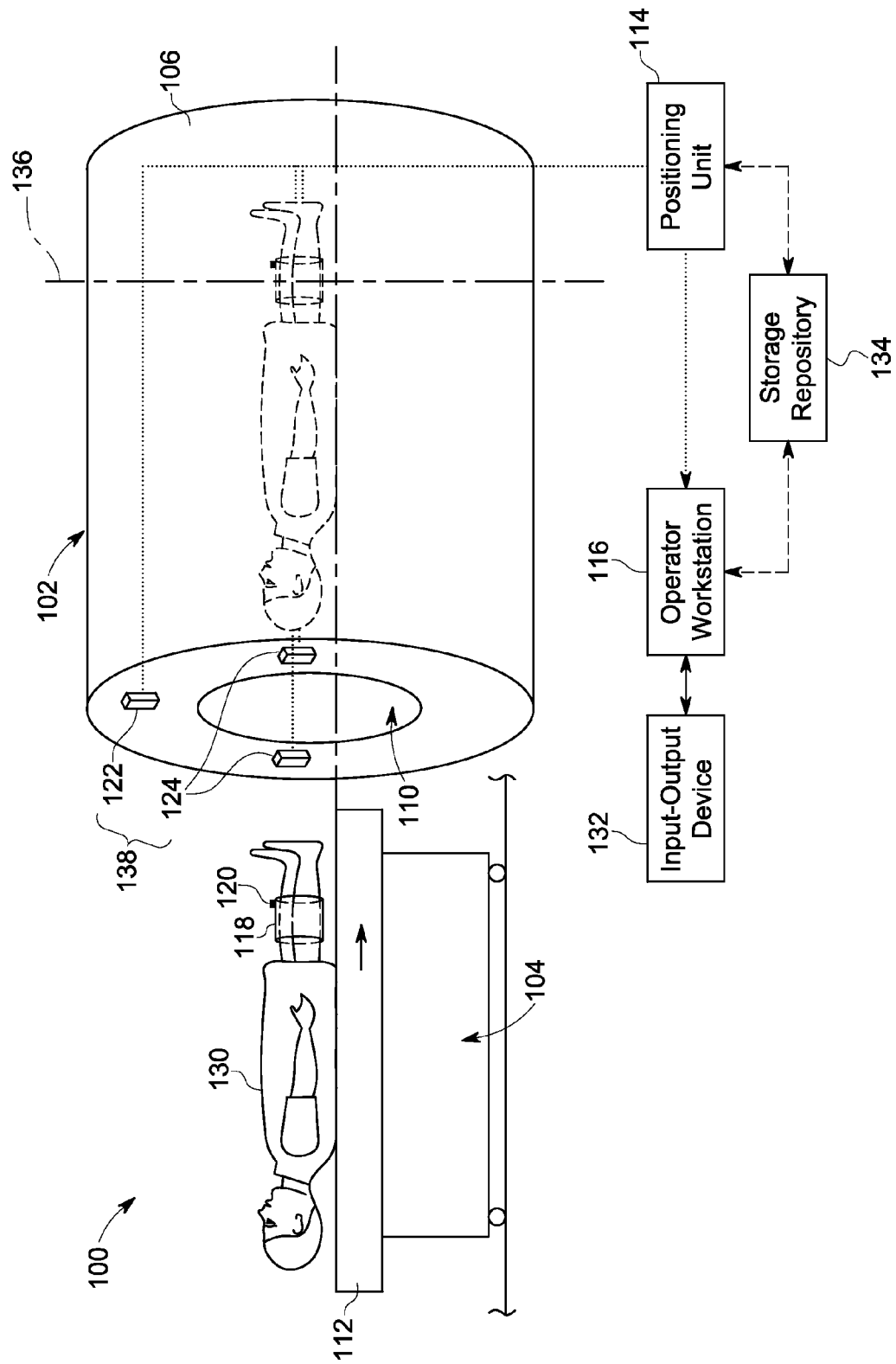
FIG. 1 is a diagram illustrating an imaging system in which landmark correction in accordance with various embodiments is implemented.

The following detailed description of certain embodiments will be better understood when read in conjunction with the appended drawings. To the extent that the figures illustrate diagrams of the functional blocks of various embodiments, the functional blocks are not necessarily indicative of the division between hardware. Thus, for example, one or more of the functional blocks may be implemented in a single piece of hardware or multiple pieces of hardware. It should be understood that the various embodiments are not limited to the arrangements and instrumentality shown in the drawings. Additionally, the system blocks in the various figures or the steps of the methods may be rearranged or reconfigured.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide for landmark correction in Magnetic Resonance Imaging (MRI) exams. In particular, various embodiments detect an improper patient landmark, compute an offset to the correct landmark, and apply the offset in subsequent imaging to correct the deficient landmark. In some embodiments, this process may also include automatically advancing the patient to the correct landmark position, for example, in systems with a limited field of view or a specialty system that scans only a certain part of the anatomy. Additionally, various embodiments may provide notifications to an operator, for example, if the desired volume to be imaged is not entirely within a desired or ideal three-dimensional (3D) field of view of the MRI system. The operator then may reposition the patient, increase the field-of-view, or the system may automatically increase the field of view. Alternatively, if a determination is made that the desired volume is not within a desired or ideal three-dimensional (3D) field-of-view of the MRI system, then one or more embodiments may compute the approximate position of the anatomy-of-interest and affect an automatic repositioning of the patient, repeating the process until the desired volume to be imaged is entirely within the desired or ideal 3D field-of-view. At least one technical effect of various embodiments is automatic landmark correction that provides repeatable, consistent and/or ideal patient landmarks, such as for systems lacking table control.

FIG. 1 illustrates an exemplary system 100 that may include automatic landmark correction of an object or subject to be imaged, such as a patient 130. The system 100 is described herein with reference to patient preparation in a Magnetic Resonance (MR) imaging operation. However, the various embodiments may be implemented in connection with different types of MRI systems or other diagnostic imaging systems. In the illustrated embodiment, the system 100 includes a magnetostatic field generator 102 operatively coupled to a motorized table unit 104 (also referred to as the table 104). The magnetostatic field generator 102 includes a magnet 106 and also RF or gradient coils and a bore 110 to receive the patient 130 therein, which in one embodiment, is disposed in a supine position. In other embodiments, however, the patient 130 may be disposed in other positions suitable for imaging.

The table unit 104 also includes a cradle 112 that supports and translates the patient 130 into the bore 110. In particular, in some embodiments, the table unit 104 includes a positioning unit 114 that controls motion of the cradle 112, and thus, the patient position within the magnet 106. The positioning unit 114, for example, controls patient position based on operator inputs, specific exam requirements and/or designated scanning protocols. Accordingly, in certain embodiments, the positioning unit 114 includes devices such as one or more digital signal processors, microcomputers, microcontrollers, Application Specific Integrated Circuits (ASICs), Field Programmable Gate Arrays (FPGA), or one or more general-purpose or application-specific processors in communication with the system 100.

In another embodiment, the table 104 or cradle 112 may also be a manually controlled table that the operator advances into the magnet bore 106. In this embodiment, the positioning unit 114 may control indicator devices, such as indicator lights or an input-output device 132 (e.g., an outputs display device), to inform the operator as to the correct positioning of the cradle 112. Such a case would be found, for example, in specialty MR systems that image only a specific anatomy.

In one embodiment, the positioning unit 114 controls the patient position based on operator inputs received through the input-output device 132 coupled to an operator workstation 116. The input-output device 132, for example, includes a display having a graphical user interface (GUI) or a switching subsystem for allowing the operator to select the desired scanning parameters and the desired ROI such as the patient's knee or spine via the GUI. Alternatively, in some embodiments, the positioning unit 114 controls the patient position based on scanning parameters (e.g., an automatic scan prescription), such as specified in a configuration file received from a data storage or database, illustrated as a storage repository 134. The storage repository 134, for example, includes a random access memory, a read only memory, a disc drive, solid-state memory device, and/or a flash memory communicatively coupled to the system 100.

The positioning unit 114, upon receiving the scanning parameters, automatically advances the cradle 112 into the bore 110, for example, using a table motor controller (not shown), and performs landmark operations as described herein. However, in other embodiments, the cradle 112 is manually advanced into the bore 110 by an operator. In either configuration, as described in more detail herein, landmark correction of either the automatic landmarking process or manual landmarking process is provided. Thus, an initial landmarking (e.g., an initial landmark position) may be corrected.

Figure 2:
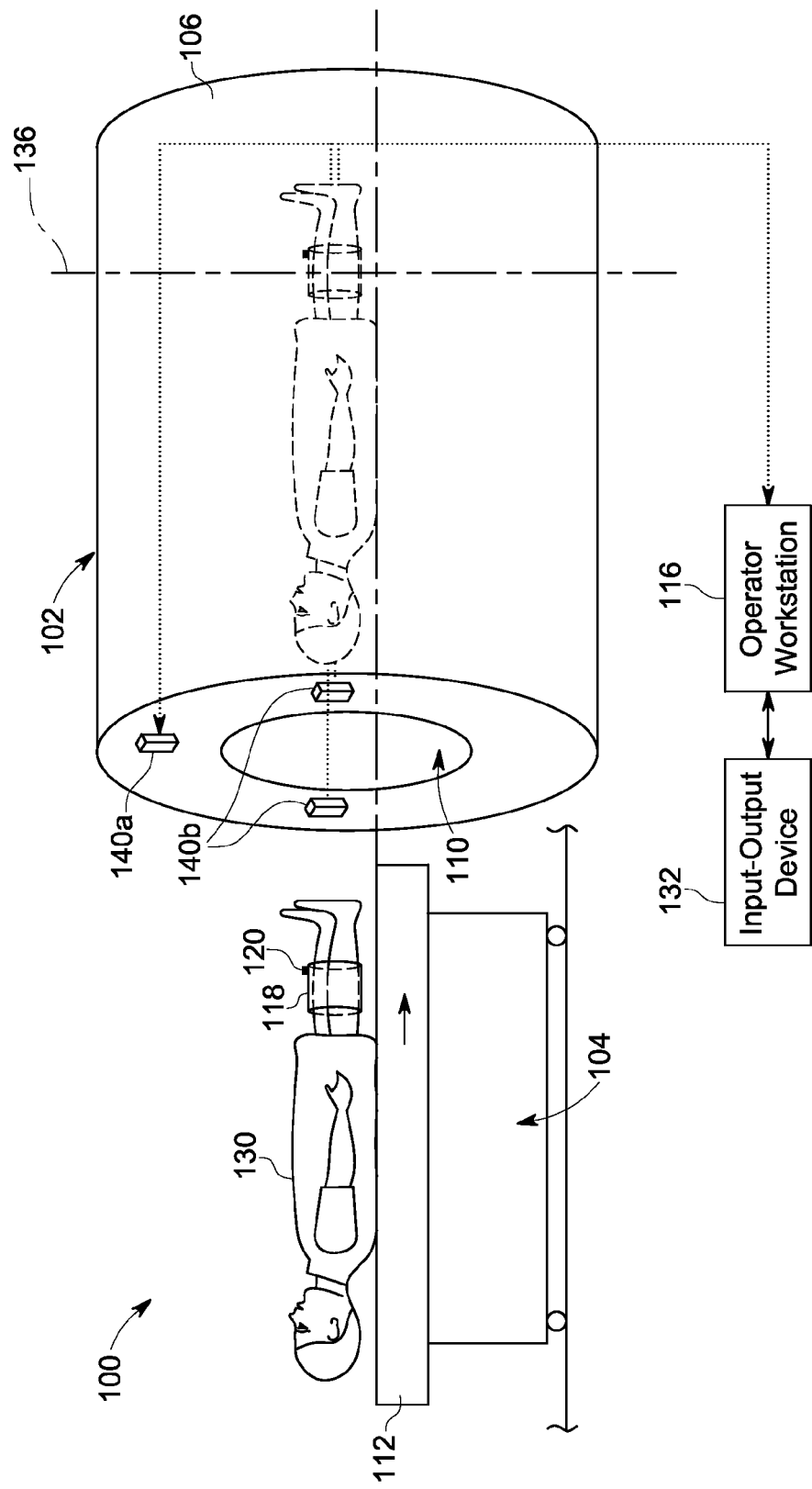
FIG. 2 is a diagram illustrating another embodiment of the imaging system of FIG. 1 in which landmark correction in accordance with various embodiments is implemented.

In the manual landmarking case, which may be performed using the system 100 shown in FIG. 2, once the patient 130 is positioned on the cradle 112, one or more alignment devices 140, which may be one or more laser alignment lights or other light sources, are turned on. It should be noted that the alignment device 140a may include axial and sagittal alignment light sources and the alignment devices 140b may include coronal alignment light sources. Thus, the alignment devices 140 in one embodiment may be light sources that project light from the opening or entrance of the bore 110 and used to landmark the patient 130 prior to scanning. For example, in one embodiment, the operator moves the cradle 112 into the magnet bore 106 until the desired ROI (illustrated as a knee of the patient 130) is positioned within (e.g., under and/or between) the alignment devices 140. The operator then may push a landmark button on the input-output device 132 to register the patient 130 with a coordinate system of the system 100 and advances the patient 130 to a scan position (illustrated by the patient 130 shown in dashed lines within the bore 106), which positions the region that was landmarked in the iso-center 136 of the magnet 106, characterized by the best field homogeneity. For example, the patient 130 is then moved into the magnet bore 110 in a feet-first orientation. The patient 130, however, can be positioned in either a head-first or the feet-first orientation depending upon the desired ROI of the patient 130 to be imaged.

The operator then initiates a landmark correction process, for example by pushing a "landmark correction" button on the input-output device 132 as described in more detail herein, which is followed by a patient scan that may be started, for example by pushing a "start scan" button on the input-output device 132. Thus, the manual landmarking in this embodiment initially includes operator intervention, including manually moving the cradle 112.

It should be noted that the various operations may be initiated using different controls of the input-output device 132, which may be physical controls or virtual controls, such as displayed on a display, which may be a touchscreen. Thus, as used herein, a button may include a hard control, a soft control (e.g., a button displayed on a screen and selectable by a user device, such as with a keyboard or mouse) or a virtual control (e.g., a displayed button selectable by touching the screen on which the button is displayed).

In the automatic landmarking case, which may be performed using the system 100 shown in FIG. 1, the positioning unit 114 automatically detects a position of an RF coil 118 positioned on the desired ROI of the patient 130. For example, the RF coil 118 may be positioned on a knee of the patient 130 (as illustrated in FIG. 1) before translating the patient 130 into the magnet bore 110. The patient 130 is then moved into the magnet bore 110 in a feet-first orientation. The patient 130, however, can be positioned in either a head-first or the feet-first orientation depending upon the desired ROI of the patient 130 to be imaged. Brain exams, for example, may be performed with the patient 130 in the head-first orientation, while lower chest and abdominal studies may be performed with the patient 130 in the feet-first orientation.

It also should be noted that in some specialty MR systems, there may not be a manual or automatic landmarking process as only a specific anatomy is scanned. In such as case, the patient is manually advanced into the magnet bore 106. After the initial scout scans, the autocorrecting landmark process in accordance with one or more embodiments is initiated to obtain the correct patient positioning.

In the embodiment of FIG. 1, the system 100 automatically initially landmarks the patient 130 for a selected imaging protocol. For example, automatic landmarking may be provided as described in co-pending U.S. patent application Ser. No. 13/332,977, entitled "Systems and Methods for Automatic Landmarking", which is commonly owned. In general, the system 100 in some embodiments automatically landmarks and scans, for example, the knee of the patient 130 using a one-touch operation. For example, the system 100 includes at least one marker 120 embedded or positioned on the RF coil 118 (e.g., a strip of reflective sheeting) or placed directly on the region of interest of the patient 130 to allow for automatic landmarking of the desired ROI. The marker 120, for example, may be positioned at the superior/inferior (S/I) center, the S/I extents, or any other suitable position on the RF coil 118. In another embodiment, multiple markers may be positioned along the length of the RF coil 118 allowing selective activation of one or more markers based on a scan prescription or configuration file. In a cardiac exam, for example, the positioning unit 114 selectively activates one or more markers disposed close to the heart of the patient 130.

In some embodiments, the marker 120 includes one or more passive and/or active elements. For example, the marker 120 may include an infrared (IR) light emitting device (LED) disposed on the exterior of the RF coil 118. In another embodiment, the marker 120 may include a radio frequency identification (RFID) chip embedded in the RF coil 118. In a further embodiment, the marker 120 may include a secondary tuned RF coil attached to the RF coil 118. Additionally, in some embodiments, where the marker 120 is implemented as an active device, the positioning unit 114 may control the marker 120 such that the marker 120 is activated during cradle travel to allow automatic landmarking, but is disabled during imaging.

The system 100 also may include an emitter and/or detector assembly 138 for detecting the marker 120 while the patient 130 is moving into the magnet bore 110. For example, the emitter-detector assembly 138 may be mounted on a front surface or within the bore 110 of the magnet 106. Additionally, in some embodiments, the emitter-detector assembly 138 includes one or more active elements that obtain a response from the marker 120, in turn making the marker 120 acoustically and/or electromagnetically detectable.

In one embodiment, for example, a secondary tuned coil detects signal from the patient 130 or from a secondary source of signal, such as a vial filled with liquid attached to the RF coil 118, only when RF coil 118 overlaps with the tuned RF coil marker 120. In this embodiment, either of the primary and the secondary tuned coils is of a design that increases precision of the localization via alignment of the coils. For example, the primary or the secondary tuned coil may have a shape designed to generate a sharp null, for example a figure "8" shape, when the coils are aligned. In an alternative embodiment, however, the emitter-detector assembly 138 includes one or more passive elements to detect the marker 120, for example, an 8 millimeter reflective strip such as made from Scotchlite, available from 3M, which includes high gain reflective sheeting.

In one embodiment, the emitter-detector assembly 138 may include the emitter 122, for example, an LED source directed towards the cradle 112 such that emitted radiation reflects off the reflective tape marker 120 and is detected by a detector 124 in the emitter-detector assembly 138. In one embodiment, both the emitter 122 and the detector 124 may be mounted in parallel on the front surface of the magnet 106 such that resulting electromagnetic emissions reflect off the reflective tape marker 120 back to the detector 124 when the marker 120 reaches a detectable position. Additionally, in certain embodiments, the radiation may be modulated and encoded, for example, using a 38 kHz type modulation, and/or digital stream pickup of 1's and 0's to facilitate detection.

The positioning unit 114, on detecting the marker 120, configures one or more position encoders (not shown) associated with the table unit 104 to sense, for example, a longitudinal position of the cradle 112 within the magnet 106. In certain embodiments, a distance from the detector 124 to the iso-center 136 of the magnet 106 may be known. Alternatively, the positioning unit 114 may receive the distance information from a configuration file received from the storage repository 134 at the beginning or during the scan. The positioning unit 114 adds this distance to the measured cradle position to determine the distance of the cradle 112 to the iso-center 136 of the magnet 106.

In some embodiments, the positioning unit 114 accounts for any offset of the marker 120 from the center of the RF coil 118 for computing the landmark position. In one embodiment, for example, the marker 120 is positioned on one side of the RF coil 118 rather than in the center of the RF coil 118 for operational convenience. Accordingly, the positioning unit 114 determines the offset of the marker 120 from the center of the RF coil 118 and updates the value of the determined distance between the cradle 112 and the iso-center 136. The positioning unit 114 then advances the cradle 112 to the iso-center 136 and automatically sets a landmark.

Figure 3:
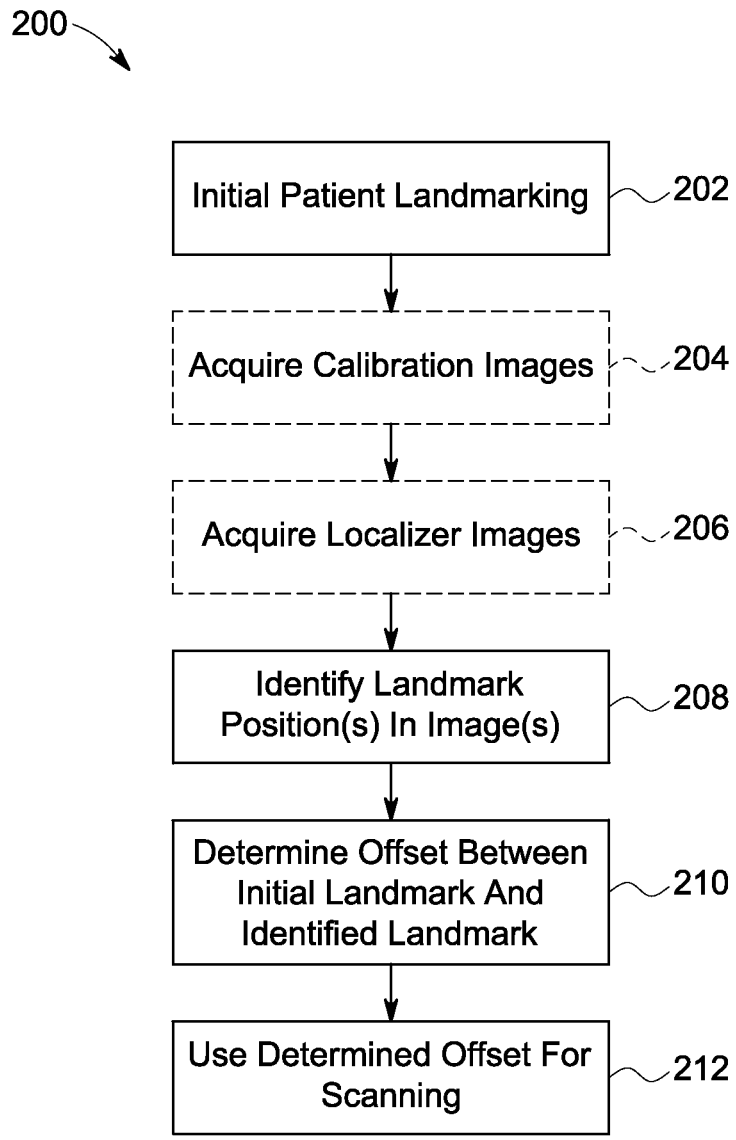
FIG. 3 is a flowchart of a method for landmark correction in accordance with an embodiment.

Various embodiments for landmark correction will now be described. In particular, various embodiments correct for the initial landmarking, such that a correction offset from the initial landmark position is determined before performing the patient scan. In one embodiment, a method 200 as shown in FIG. 3 may be provided for landmark correction. The method 200 includes performing an initial patient landmarking at 202. For example, automatic landmarking or manual landmarking of the patient may be performed as described in more detail herein.

The method 200 then includes obtaining images to be used for landmark correction as described below. In particular, at 204, calibration images are optionally obtained, which may be performed automatically or manually. For example, in MR scans with parallel imaging, a scout scan that spans a large region of an anatomy of a patient is obtained as part of a "calibration" scan to acquire the calibration images. It should be noted that the calibration images may be acquired using any suitable process.

The method 200 also includes at 206 optionally acquiring localizer images, which may be performed automatically or manually. The localizer images may be used in localizing the anatomical region of interest. The localizer images may be acquired employing a single modality imaging system. For example, the localizer images representative of the anatomical region of interest in the patient may be acquired using an MRI system. The localizer images may be used to ensure that the anatomical region of interest, such as the cardiac region, for example, is located within the field of view of the one or more localizer images. The term field of view is used in various embodiments to refer to physical dimensions of acquisition. For example, images or image volumes representative of a thoracic and/or cardiac region of the patient may be acquired such that the images include the heart. The localizer images may include scout images, locators, scanograms, plan scans, and the like. Diagnostic images are generally of higher quality and that have diagnostic values useful for clinical diagnosis.

In various embodiments, a 2D localizer image or a 3D localizer image may be acquired. The localizer images may be obtained in a sagittal plane, a coronal plane, an axial plane, or in any plane or combination thereof. Further, any pulse sequence may be used to obtain these localizer images.

It should be noted that the one or more localizer images may also be acquired using a different single modality imaging system (e.g., a Computed Tomography (CT) imaging system) or a multi-modality imaging system. The multi-modality imaging system may include for example, a Positron Emission Tomography (PET)-MRI imaging system, among other modalities. It should be noted that if the localizer images are acquired using a multi-modality imaging system, a feature space in each of the acquired localizer images may be standardized in order to match data in the multi-modal space.

Using the calibration and/or localizer images, one or more landmark positions in the images are determined at 208. For example, based on the particular region of interest, such as the anatomy of interest, one or more landmark positions may be determined as described in more detail herein. In general, the localizer images may be processed, such as using suitable image segmentation or other decomposition methods to identify specific patient anatomy, which is then used to identify one or more landmark positions, which may be one or more of a determined set of ideal landmark positions. Thus, in some embodiments segmentation of the localizer images identifies sub-anatomies with the patient's body. Based on known relationships of the sub-anatomies (e.g., relative locations in the body) or heuristics or other measurements, one or more desired or ideal landmarks are determined. Accordingly, in some embodiments, correction may be provided by recognizing or identifying imaged landmarks and then choosing and ideal landmark, such as a midpoint between two identified landmarks (e.g., two bones).

Thereafter, an offset between the initial landmark and the identified landmark is computed at 210. For example, a difference in the location of the landmark from the initial landmarking and the desired or ideal landmark determined from the calibration and/or localizer images is determined. For example, using the one or more calibration and/or localizer images, these images may be compared with images from the initial patient landmarking. The comparison determines any differences between the calibration and/or localizer images and the initial landmark. For example, a pixel by pixel comparison of the images may be performed to determine an offset between the current and desired or ideal landmark(s).

The determined offset is then used during a patient scan at 212. For example, the offset determined at 210 may be added to:

a. the prescribed position of additional localizer images used to compute an automatic scan plane prescription;

b. the prescribed position of diagnostic images; or c. the established (zeroed) patient landmark is a new baseline location, which would move the patient to that location.

Thus, the offset may be used to correct for an initial landmarking (e.g., an initial landmark position) or move the patient to a desired or optimal position of the patient and/or the patient table for imaging the desired anatomical region of interest in the patient. The desired, optimal or ideal position may generally be representative of a position of the patient and/or the patient table that allows the anatomical region of interest to be centered with respect to a portion of the MRI system. In some embodiments, this position may be representative of a position of the patient within the patient bore of the MRI system that allows imaging of enhanced quality of the anatomical region of interest.

Figure 4:
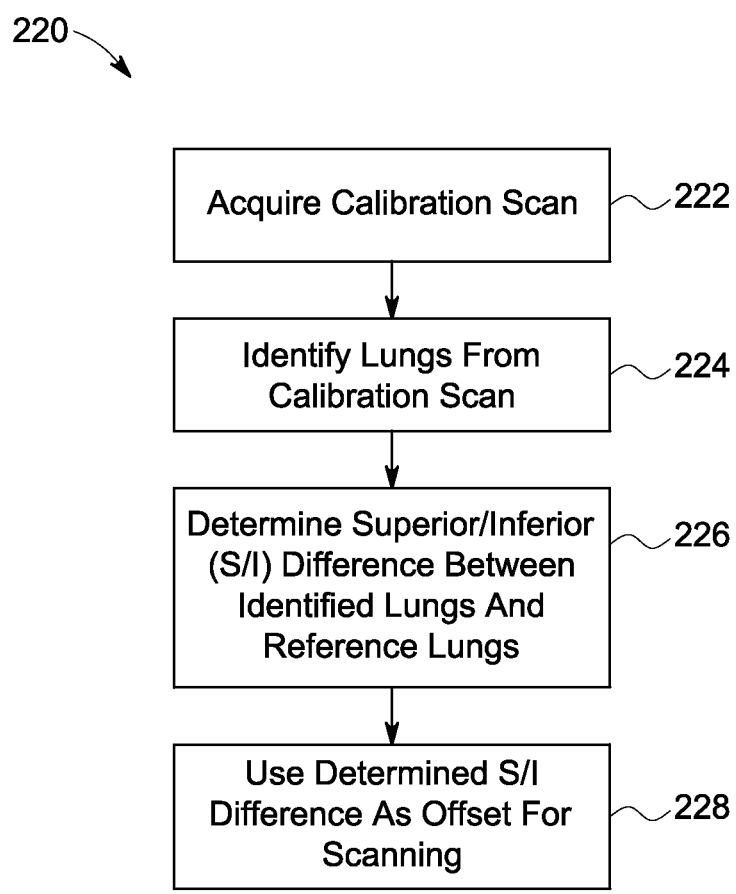
FIG. 4 is a flowchart of a method for landmark correction in accordance with another embodiment.

Different examples and applications of landmark correction of various embodiments will now be described. In particular, FIG. 4 illustrates a method 220 for landmark correction in a cardiac application. The method includes acquiring a calibration scan at 222, which may be performed as described in more detail herein. Thereafter, using images from the calibration scan, the lungs of the patient are identified or segmented at 224. For example, the lungs will show up as a pair of large dark objects in the scan protocol. In various embodiments, the images may be algorithmically searched for the dark paired objected with the shape and size characteristics corresponding to human lungs.

Thereafter, at 226, the superior/inferior (S/I) difference between the identified lungs from the calibration scan and reference lungs is computed. For example, a difference in the distance between the location of the lungs in the calibration scan images and reference lungs may be calculated using any suitable image distance measuring technique. The reference lungs may be in a reference image representative of a previously acquired image corresponding to the region being imaged, which in this embodiment is the heart. Thus, for imaging the cardiac region in the patient, the reference image may include a previously acquired image corresponding to the cardiac region. For example, the reference image may be stored in a reference image database that includes images from different patients (e.g., different image atlases or models). It should be noted that the reference image(s) used may be normalized across patient size and/or shape or a particular reference image selected based on the patient being imaged may be used.

Thus, the determined S/I offset distance is representative of the physical distance between initial landmark position(s) and a desired or ideal landmark position(s).

It should be noted that in various embodiments the term "reference" as used herein, such as reference objects or images, such as reference lungs may refer to different types of reference information or data. For example, a reference may be a model or atlas. In some embodiments, for example, a geometric model may be matched against landmarks as follows:
  a. Landmarks are identified individually on incoming data (e.g., by feature analysis/segmentation); and
  b. Once point landmarks are found, the landmarks are matched against a geometric model.

In other embodiments, for example, a statistical atlas generated from ground truth data may be matched against incoming data, such that matching is performed simultaneously and in an image space approach.

The determined S/I difference is then used as an offset for scanning and/or image formation at 228. For example, diagnostic cardiac images may be acquired using the computed S/I offset as described herein, which may include correcting for the offset when generating images or moving the patient within the bore (e.g., moving the patient table left/right) in accordance with a distance corresponding to the S/I offset.

Figure 5:
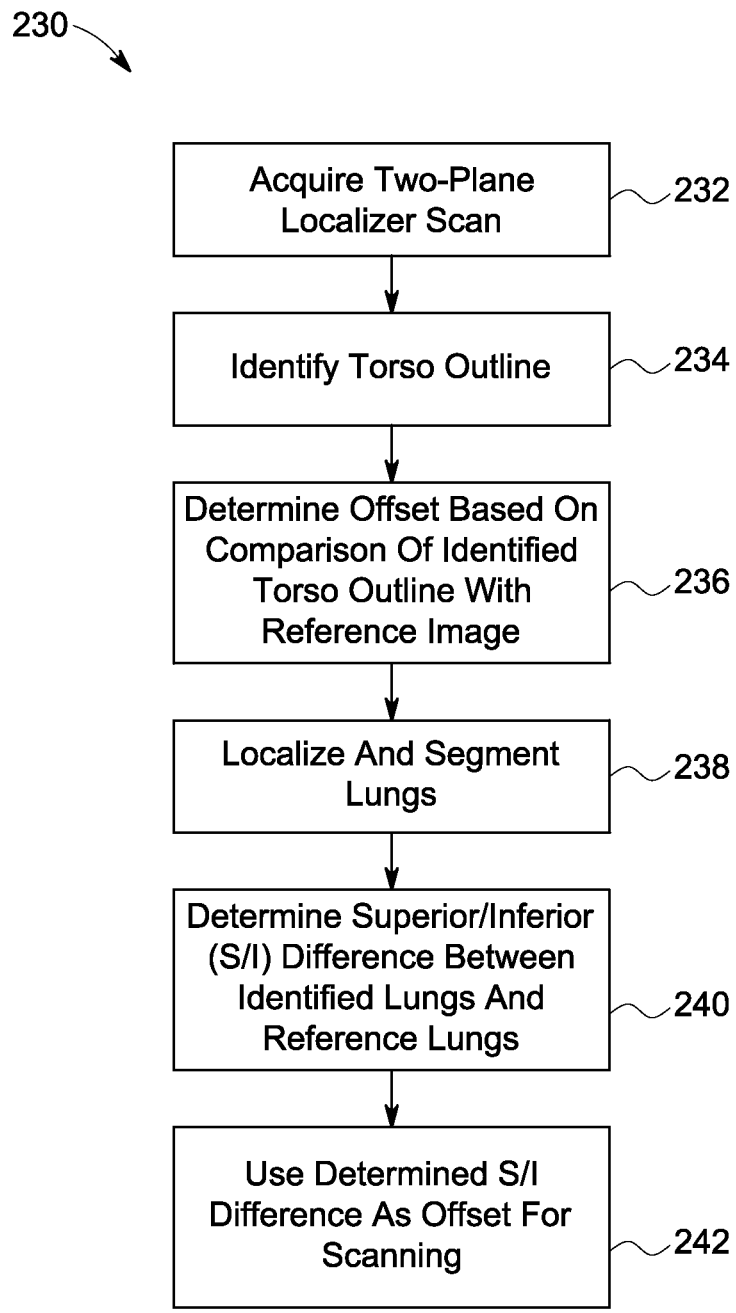
FIG. 5 is a flowchart of a method for landmark correction in accordance with another embodiment.

As another example, a method 230 as shown in FIG. 5 may be provided for landmark correction in a cardiac application without calibration. In this embodiment, the patient is positioned on a patient table of the MRI system and one or more imaging coils may be positioned on the patient as described herein. For imaging the cardiac region in the patient, the imaging coils may be positioned on or around the cardiac region of the patient. The patient may then be positioned within the patient bore of the MRI system. For cardiac MRI, it may be desirable to position the patient within the patient bore such that the cardiac region of the patient is centered with respect to the magnet in the MRI system.

In this embodiment, then, one or more localizer images may be obtained. The one or more localizer images may be used to ensure that the anatomical region of interest lies within the field of view of the acquired localizer images. In one embodiment, a two-plane localizer scan is performed at 232, such that the localizer images may include a two-plane localizer image. In particular, the two plane localizer image may include two two-dimensional (2D) image slices. Specifically, one of the two 2D image slices may include a 2D image slice acquired along an axial direction, while the other 2D image slice may include a 2D image slice acquired along a coronal direction. These localizer images may be acquired such that image data corresponding to a relatively large (large enough) field of view data in two planes is obtained. Specifically, image data may be acquired in the two planes to ensure that the anatomical region of interest is within the two planes, which in one embodiment includes 2D image slices along the axial and coronal orientations.

Then at 234, the torso outline of the patient is identified. In particular, an outline of the torso of the patient may be computed using the axial 2D image slice using any suitable method. The computed torso outline provides a first step in the localization. For example, for imaging the cardiac region, the lungs of the patient may be localized.

An offset is then determined at 236 based on a comparison of the identified torso outline and a reference, such as a reference image. For example, in one embodiment, an anterior-posterior (AP) and/or a left-right (LR) offset are both determined. Thus, an offset between the axial image and the reference image may include an offset in AP direction and/or in a LR direction. In one embodiment, the computed torso outline may be compared with a previously stored reference image that corresponds to the computed torso outline. In addition, the reference image may be scaled based on the computed torso outline. This scaling facilitates normalizing across patient size and/or shape. For example, if the computed torso outline of the patient under observation is larger than the torso outline of the reference image, then the reference image may be scaled up to match the computed torso outline. However, if the computed torso outline of the patient under observation is smaller than the torso outline of the reference image, then the reference image may be scaled down to match the computed torso outline.

Once the offset is determined, a determination may be made to verify if the offset is greater than or less than a determined threshold. The determined threshold may be representative of an acceptable offset between the computed torso outline and the reference torso outline. Accordingly, a determination may be made as to whether the offset is greater than the determined threshold. If the offset is greater than the determined threshold, then the position of the patient, the patient table, or both the patient and the patient table may be adjusted based on the determined offset. For example, the patient and/or the patient table may be translated along the AP direction to compensate for any offset in the AP direction. Similarly, any offset in the LR direction may be compensated for by adjusting the position of the patient on the patient table. Adjusting the position of the patient and/or the patient table to compensate for any offset facilitates centering the torso of the patient within the desired region of acquisition. Thereafter, a new torso-centered coronal image may be acquired. In particular, a coronal image of the torso of the patient that is centered within the desired region of acquisition may be acquired.

Then the desired anatomical region of interest may be localized based on the torso-centered coronal image. For example, if the anatomical region of interest includes the heart, then the cardiac region may be localized using the torso-centered coronal image. In one example, the torso-centered coronal image of the cardiac/thoracic region of the patient may be used to localize and segment the lungs at 238. The lungs may be identified by determining large dark objects in the torso-centered coronal image, in one embodiment. Once the lungs are identified, the cardiac region may be identified based on a prior modeling of the cardiac region's geometric relationship with the lungs, using a reference image database as described herein.

The method also includes determining an S/I difference between the identified lungs from the localizing and segmenting and a corresponding reference image. The reference image may be an image based on an initial landmarking as described herein or may be, for example, an atlas image. Thus, if the desired anatomical region of interest includes the cardiac region, an image of the cardiac region may be acquired and compared with a reference image of the cardiac region to generate an S/I difference image. It should be noted that the acquired image may be the torso-centered coronal image. However, in other embodiments, the acquired image may be other types of localizer scan images.

The determined S/I difference then may be used at 242 as an offset for scanning or image formation, such as to provide landmark correction in image generation or for use in moving the patient. Thus, the SI difference may be used to provide the optimal or desired position of the patient and/or the patient table, such as a position of the patient and/or the patient table that allows the anatomical region of interest to be centered in the MRI system. In one embodiment, the desired position may include a position of the patient and/or the patient table such that the anatomical region of interest is centered in the middle of the MRI system. In other embodiments, the desired position may include a position of the patient and/or the patient table such that the anatomical region of interest is aligned or centered with respect to a position of the magnet of the MRI system. For example, as described herein, when performing a cardiac MRI exam, the desired or optimal position may be representative of a position of the patient and/or patient table such that the heart of the patient is centered in the middle of the MRI system.

In some embodiments, the user may be provided guidance to move the patient and/or patient table to the desired location, for example, using on-screen notifications, which may provide feedback as the operator manually moves the table. In other embodiments, the patient table may be moved automatically to locate the anatomical region of interest of the patient at the desired position.

It should be noted that the localizer images may be acquired by the MRI system in some embodiments. However, in other embodiments, an image acquisition device, such as a CCD camera may be used to acquire one or more localizer images.

Figure 6:
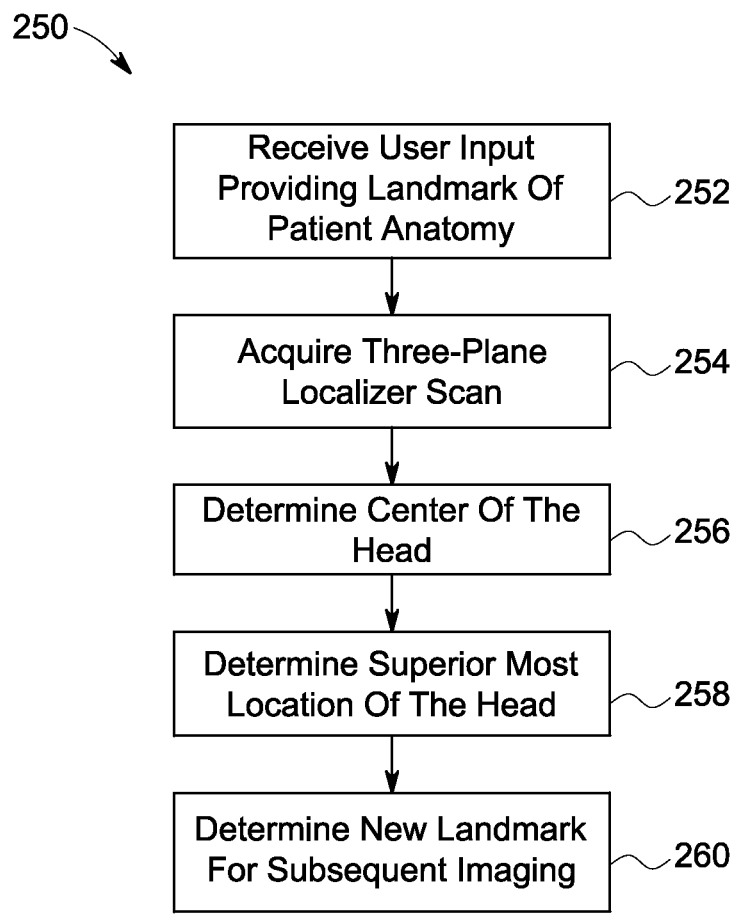
FIG. 6 is a flowchart of a method for landmark correction in accordance with another embodiment.

As another example, a method 250 as shown in FIG. 6 may be provided for landmark correction in a neurology application. The method 250 includes receiving at 252 a user input providing a landmark of a patient anatomy. For example, before image acquisition, the user may provide a rough landmark of the patient anatomy that will be moved to the center of the magnet for imaging. Thereafter, at least one image of a head of a subject is obtained through an imaging device. In one embodiment, a three-plane localizer scan may be performed to acquire a three-dimensional (3D) localizer image at 254. However, in other embodiments, 2D localizer images may be acquired. The localizer images may be obtained, for example, in the sagittal plane, coronal plane, axial plane, or in any other plane or a combination thereof. Further, any pulse sequence may be used to obtain these localizer images. In another embodiment, at least one image obtained may be an optical image. In one example, a sagittal image and/or a coronal image may be obtained as the one or more localizer images.

The center of the patient's head is then determined at 256 from the localizer images. For example, an axial localizer image may be used to determine the center of the head in the LR and AP directions, such as by determining a middle point therebetween. A superior most location of the head is also determined at 258. For example, sagittal and coronal localizer images may be used to determine the superior most location of the head. It should be noted that any suitable image processing algorithm may be performed on the localizer images to identify a particular feature associated with the head, such as the center or superior most location of the head. In some embodiments, any image processing algorithm, such as using image intensity statistics, for example, maximum intensity or mean intensity, etc., may be used to separate signal from noise to identify a feature associated with the head.

Based on the determination of the superior most location of the head, a new landmark is determined for subsequent imaging at 260. This new landmark together with the determined center of the head provide for coverage of the head in the S/I direction and in the axial plane. For example, an optimal position in the head may be calculated to be set as the new landmark. In a brain scan application, a landmark may be set in a transversal plane at a pre-determined distance in an inferior direction from the top of the head.

Figure 7:
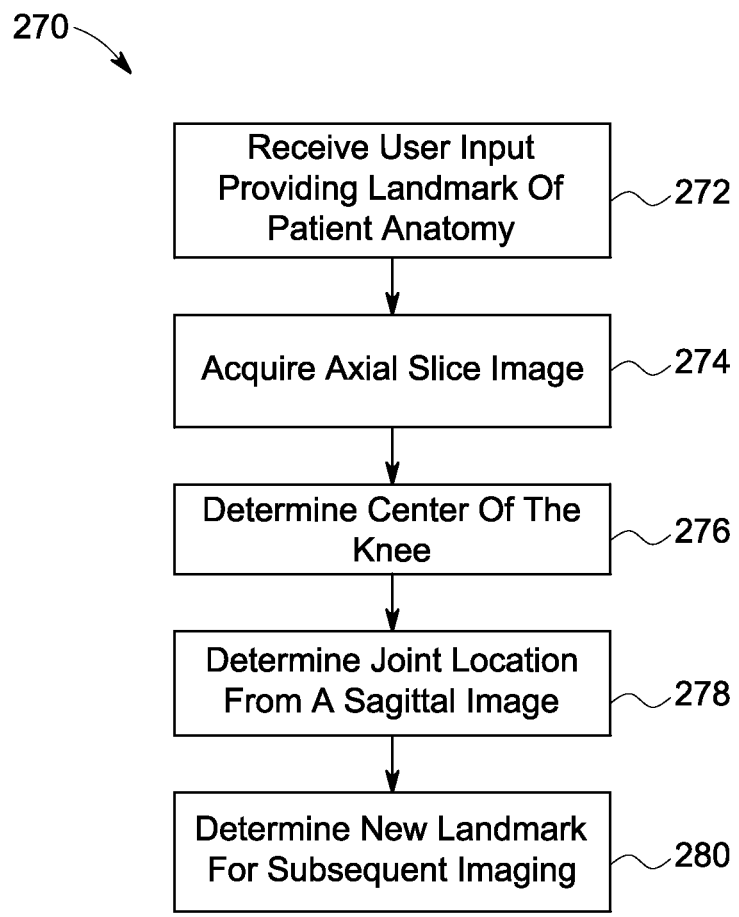
FIG. 7 is a flowchart of a method for landmark correction in accordance with another embodiment.

As another example, a method 270 as shown in FIG. 7 may be provided for landmark correction in a knee application. Similar to the method 250, a user input providing a landmark of a patient anatomy is received at 272. Thereafter, an axial slice image is acquired at 274. In particular, in one embodiment, a single axial slice image is acquired at the iso-center of the magnet with a large field of view. Using the axial image in this embodiment, a center of the knee is determined at 276. Specifically, the center of the knee to be imaged in the LR and AP directions is determined, such as by determining a midpoint in the LR and AP directions.

A joint location of the knee is then determined at 278. In particular, a single sagittal image through the LR center is acquired and the joint location is computed from the sagittal image. For example, any suitable image processing technique may be used to identify the structure corresponding to the knee joint. Based on the determination at 278, a new landmark is determined at 280 for subsequent imaging. This new landmark together with the determined center of the knee provide for coverage of the knee in the S/I direction and in the axial plane. For example, an optimal position in the knee may be calculated to be set as the new landmark.

Figure 8:
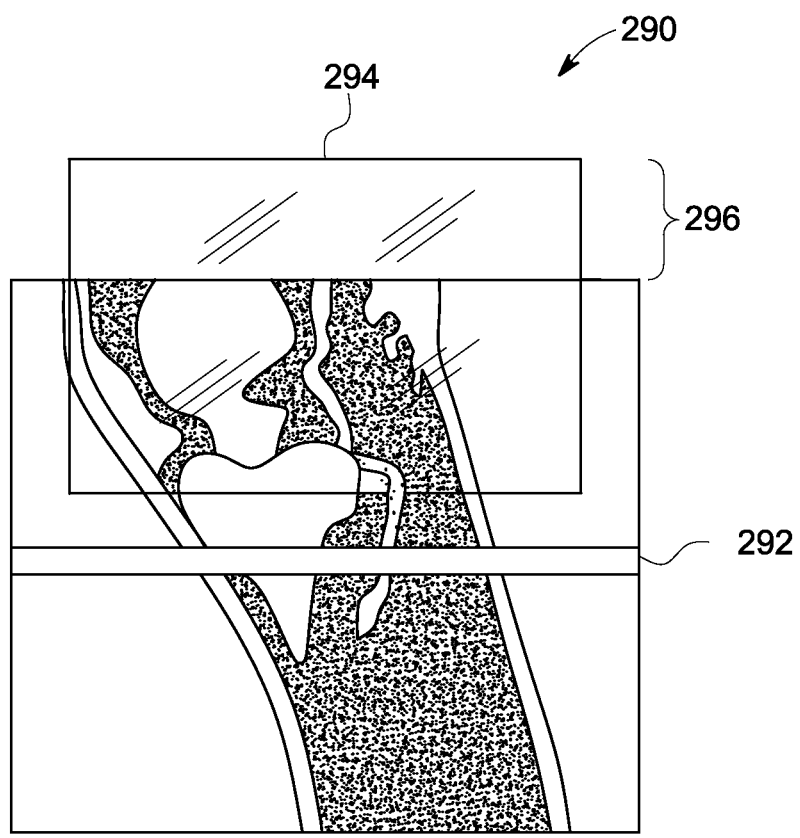
FIG. 8 is an image illustrating improper landmarking.

FIG. 8 shows an image 290 of a knee wherein the line 292 represents the landmark and the shaded region 294 represents the coverage needed for an automatic scan plane prescription. The landmark was determined by an initial landmarking as described herein. As can be seen by the region 296 (above the image 290 in FIG. 8), due to the improper initial landmark position, there are missing image slices.

In accordance with various embodiments, the image coil and patient anatomy are properly positioned in the center of the magnet or the error that resulted from the initial landmarking is corrected. For example, the landmark may be detected as the patient is moved from a home position to a magnet iso-center. Once at the iso-center, a localizer scan is performed as described herein, and then an ideal or a desired center of the scan volume is computed and used as an offset from the initial landmark position. For example, by determining the RF coil position and recognizing patient anatomy, landmarking errors (such as patient positioning errors) may be compensated or the operator can be directed to reposition the patient. Thereafter, automatic scan plane prescriptions may be used, for example.

As one example, a reflective sheeting may be coupled (e.g., affixed) to a knee coil as a marker in a defined position as described herein. An infrared (IR) LED and IR receiver module may be mounted to the front of the MRI scanner. The IR detection mechanism may be calibrated, for example, by an automatic landmarking of the coil, then manually returning to the landmark position, where the table position is adjusted until the laser light from the IR LED is coincident with the center of the coil. The offset is then used as the landmark error. This calibration process may be performed only once or at different intervals (e.g., during system maintenance).

In operation, the output from the IR receiver module is input to a processor (e.g., a microprocessor) programmed to filter the signal using suitable filtering techniques and communicate the detection signal to the MRI scanner, which may be communicated via a wired connection or a wireless connection. A scan or exam begins with the table 104 and patient 130 at the home position (which is fully outside the magnet 106 as shown in FIGS. 1 and 2). In one embodiment, when the user presses a scan button, the table 104 and patient are moved into the bore 110 as described in more detail herein. As the coil marker, for example, the marker 120 (shown in FIGS. 1 and 2) passes the emitter-detector assembly 138 (shown in FIGS. 1 and 2), in one embodiment an IR beam is reflected from the marker 120 and detected by the detectors (e.g., the detectors 124 shown in FIGS. 1 and 2). This detection generates a signal that is communicated to a scanner digital subsystem, which may form part of the operator workstation 116 (shown in FIGS. 1 and 2), which adds the pre-calculated detector-iso-center distance to the current table position and then moves the table to this new position.

Figure 9:
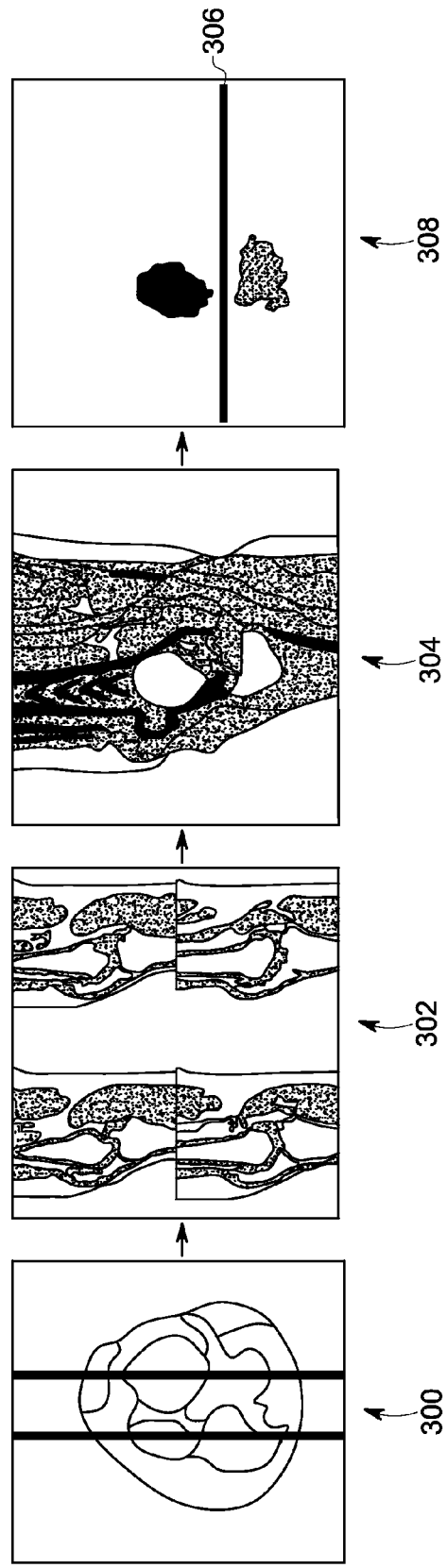
FIG. 9 shows images illustrating landmark correction in accordance with various embodiments.

Thereafter, with the center of the coil, for example, the coil 118 (shown in FIGS. 1 and 2) at the approximate iso-center, localizer images are acquired and processed to determine the scan volume center as described in more detail herein. For example, as shown in FIG. 9, a 2D axial image 300 is acquired and processed to determine the LR and AP coverage of the knee and then the LR coverage and the location of a 3D sagittal localizer are automatically determined as described herein and images 302 are acquired. The knee joint location is then computed, for example, by performing a maximum intensity pixel projection in the LR direction to identify and detect the femur and tibia as shown in the image 304, and then a center line 306 between these two bones is computed as shown in the image 308. The knee joint location is used to determine the scan volume center in the S/I direction, which may be used to further reduce errors caused by the knee not being placed in the middle of the coil.

Figure 10:
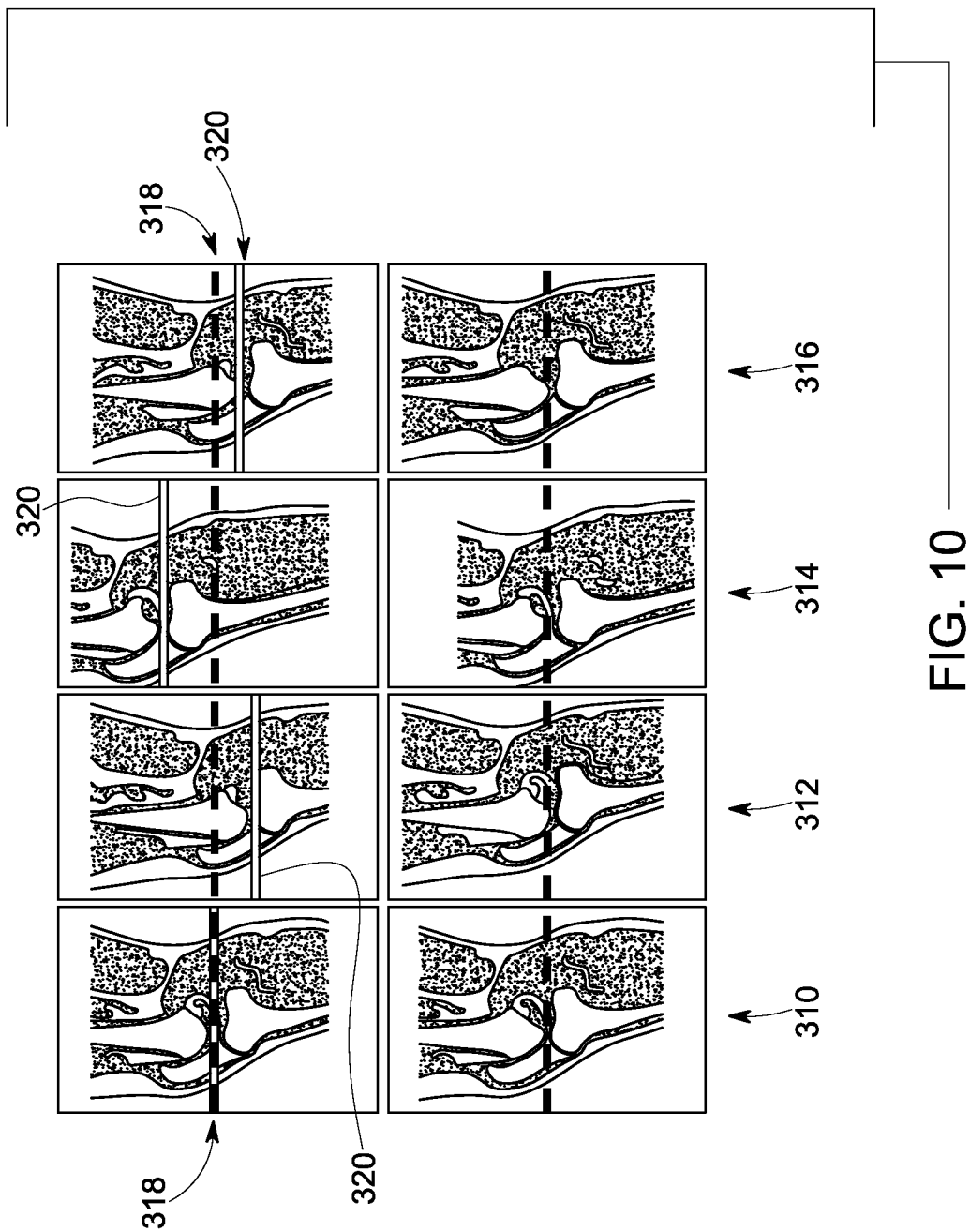
FIG. 10 shows images illustrating landmark correction in accordance with various embodiments.

FIG. 10 illustrates four vertical sets 310, 312, 314, 316 of knee images. The images 310 represent a knee properly positioned in the coil. The knee is improperly positioned in the other sets of images 312, 314, 316. The lines 318 (in the top row of images) show the location of the initial landmark and the lines 320 show the offset from the landmark computed by the center of scan volume computations in accordance with various embodiments. The bottom row of images in the sets 310, 312, 314, 316 are images acquired after applying the computed center of scan volume offset (calculated in accordance with various embodiments) to the initial landmark position. In one example, the offsets determined for the center of scan volume, from left to right are as follows: 0.5 mm, −24.9 mm, 46.3 mm and −16.1 mm.

Thus, various embodiments provide landmark correction for MRI. The landmark corrections may be applied to an initial landmark that is determined manually or automatically.

Figure 11:
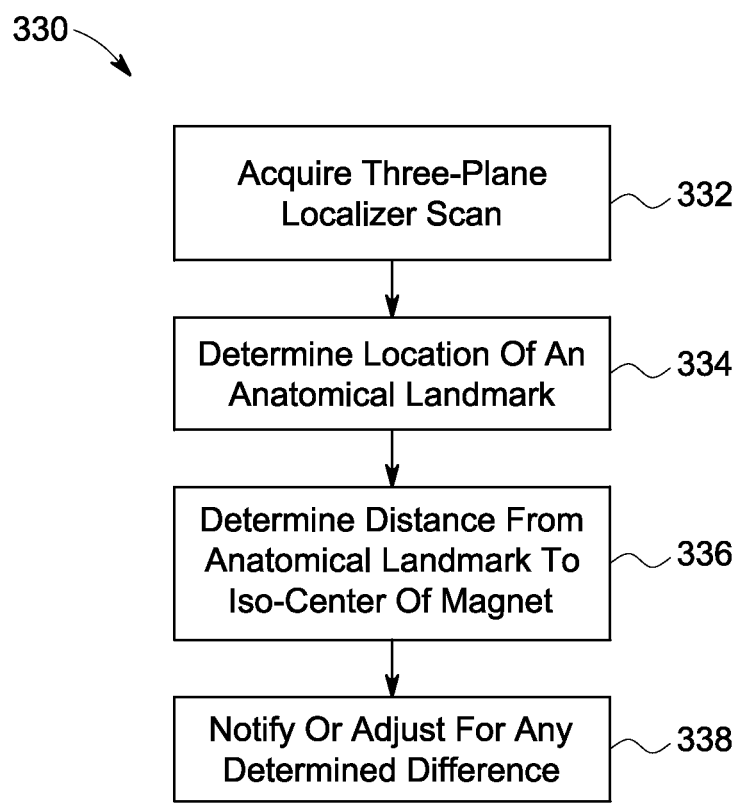
FIG. 11 is a flowchart of a method for landmark correction in accordance with another embodiment.

It should be noted that the various embodiments may be used for different types of scans with different systems and for different anatomies. For example, FIG. 11 illustrates a method 330 for landmark correction in an MRI system having a limited field of view and/or a system lacking table control. For example, in a head only MRI scanner, the method includes, before image acquisition, placing the patient in the scanner that recognizes an approximate landmark as described in more detail herein.

The method 330 specifically includes acquiring a three-plane localizer scan at 332, for example, as described in more detail herein. For example, a three-plane localizer scan may be acquired at the iso-center of the magnet with a large field of view. Then, a location of an anatomical landmark is determined at 334. For example, the localizer images are used to determine the location of an anatomical landmark in a defined list, for example, the center of the brain as described herein, the top of the head (bregma) as described herein, and/or the trapezius using a suitable detection method.

The distance from the anatomical landmark to the iso-center of the magnet is then determined at 336. This distance may be determined using any suitable measuring technique and as described in more detail herein. Then, a notification or adjustment for any determined difference may be provided at 338. For example, in one embodiment, if the distance exceeds a threshold (e.g., a predetermined threshold) then: (1) the operator may be notified (e.g., a visual or audible warning) to reposition the patient, (2) the operator may be notified to increase the field or view and/or (3) the system may automatically increase the field of view. Thus, various embodiments may notify the operator, for example, as to manually move the object based on the determined offset.

Figure 12:
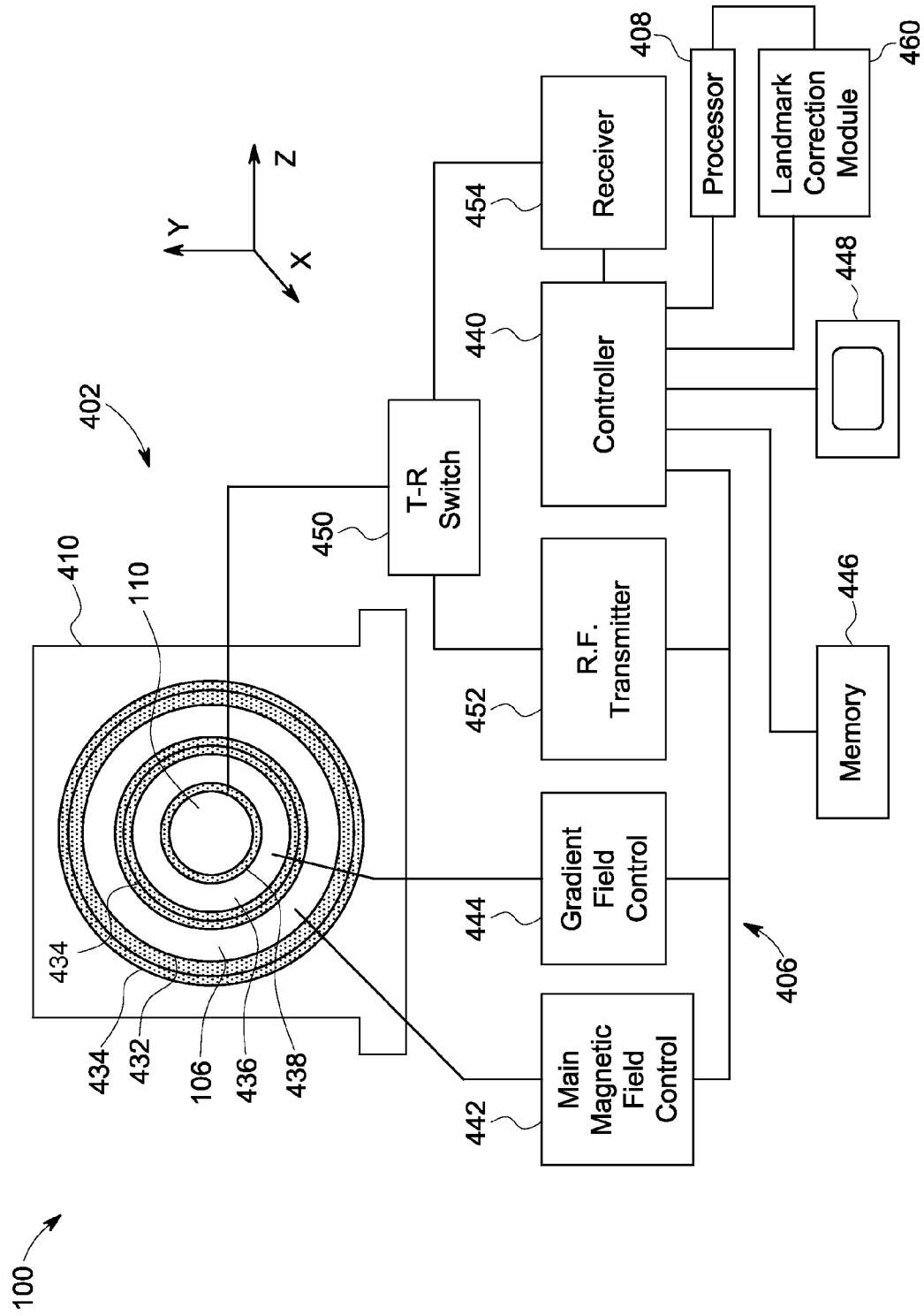
FIG. 12 is a schematic block diagram illustrating an MRI system formed in accordance with various embodiments.

As described above, the various embodiments may be implemented in connection with different types of MRI systems. For example, the system 100 may be embodied as an MRI system as shown in FIG. 12. The system 100 includes an imaging portion 402 having an imaging unit 404 (e.g., imaging scanner) and a processing portion 406 that may include a processor 408 or other computing or controller device. In particular, the imaging unit 404 enables the system 100 to scan the patient 130 (shown in FIGS. 1 and 2) to acquire image data, which may be image data of all or a portion of the object or patient 130. The imaging unit 404 includes a gantry 410 that includes one or more imaging components (e.g., magnets or magnet windings within the gantry 410) that allow acquisition of the image data. In multi-modality imaging systems, in addition to the magnet(s) for MRI, an X-ray source and detector for CT imaging, or gamma cameras for Nuclear Medicine (NM) imaging may be provided. The imaging components produce signals that represent image data that is communicated to the processing portion 406 via a communication link that may be wired or wireless. It should be noted that the signals may be configured in different protocols, scan plane prescriptions, etc. It should also be noted that during an imaging scan by the imaging unit 404, the gantry 410 and the imaging components mounted thereon or therein may remain stationary or rotate about or along a center of rotation defining an examination axis through the bore 110. The patient 130 may be positioned within the gantry 410 using, for example, the motorized table 104 (shown in FIGS. 1 and 2).

In operation an output of one or more of the imaging components is transmitted to the processing portion 406, and vice versa, which for example, may include, transmitting signals to or from the processor 408 through a control interface, such as a controller 440. The processor 408 also may generate control signals for controlling the position of the motorized table 104 or imaging components based on, for example, user inputs or a predetermined scan. During a scan, image data, such as magnetic resonance image data from the imaging components may be communicated to the processor 408 through a data interface via the control interface. The processor 408 and associated hardware and software used to acquire and process data may be collectively referred to as the operator workstation 116 (shown in FIGS. 1 and 2). The workstation 116 includes user input devices, such as a keyboard and/or other input devices such as a mouse, a pointer, and the like, and a monitor 428. The monitor 428 displays image data and may accept input from a user if a touchscreen is available.

The system 100 generally includes within the gantry 410, the magnet 106, for example, a superconducting magnet formed from coils, which may be supported on a magnet coil support structure. A helium vessel 432 (also referred to as a cryostat) surrounds the magnet 106 and may be filled with liquid helium. The liquid helium may be used to cool a cold-head sleeve and/or a thermal shield.

Thermal insulation 434 is provided surrounding the outer surface of the helium vessel 432 and the inner surface of the magnet 106. A plurality of magnetic gradient coils 436 are provided inside the superconducting magnet 430 and an RF transmit coil 438 is provided within the plurality of magnetic gradient coils 436.

In some embodiments, the RF transmit coil 438 may be replaced with a transmit and receive coil. The components within the gantry 410 generally form the imaging portion 402. It should be noted that although the magnet 106 is a cylindrical shape, other shapes of magnets can be used.

The processing portion 406 generally includes the controller 440, a main magnetic field control 442, a gradient field control 444, a memory 446, a display device 448, a transmit-receive (T-R) switch 450, an RF transmitter 452 and a receiver 454.

In operation, a body of an object, such as the patient 130 (shown in FIGS. 1 and 2) or a phantom to be imaged, is placed in the bore 412 on a suitable support, for example, a patient table, such as the table 104 (shown in FIGS. 1 and 2). The magnet 106 produces a uniform and static main magnetic field Bo across the bore 212. The strength of the electromagnetic field in the bore 412 and correspondingly in the patient 130, is controlled by the controller 440 via the main magnetic field control 442, which also controls a supply of energizing current to the superconducting magnet 430.

The magnetic gradient coils 436, which include one or more gradient coil elements, are provided so that a magnetic gradient can be imposed on the magnetic field Bo in the bore 412 within the magnet 106 in any one or more of three orthogonal directions x, y, and z. The magnetic gradient coils 436 are energized by the gradient field control 444 and are also controlled by the controller 440.

The RF transmit coil 438, which may include a plurality of coils, is arranged to transmit RF magnetic pulses and/or optionally simultaneously detect MR signals from the patient 130 if receive coil elements are not. If an receive coil is provide, the coil may be of any type or configuration, for example, a separate receive surface coil, such as a knee coil. The receive surface coil may be an array of RF coils provided within the RF transmit coil 438.

The RF transmit coil 438 and the receive surface coil are selectably interconnected to one of the RF transmitter 452 or receiver 454, respectively, by the T-R switch 450. The RF transmitter 452 and T-R switch 450 are controlled by the controller 240 such that RF field pulses or signals are generated by the RF transmitter 452 and selectively applied to the patient 130 for excitation of magnetic resonance in the patient 130. While the RF excitation pulses are being applied to the patient 130, the T-R switch 450 is also actuated to disconnect the receive surface coil from the receiver 454.

Following application of the RF pulses, the T-R switch 450 is again actuated to disconnect the RF transmit coil 438 from the RF transmitter 452 and to connect the receive surface coil to the receiver 454. The receive surface coil operates to detect or sense the MR signals resulting from the excited nuclei in the patient and communicates the MR signals to the receiver 454. These detected MR signals are in turn communicated to the controller 440. The controller 440 includes a processor (e.g., image reconstruction processor), for example, that controls the processing of the MR signals to produce signals representative of an image of the patient 130, which may include applying a landmark correction offset from a landmark correction module 460, which may determine landmark correction offsets in accordance with various embodiments as described herein. It should be noted that the landmark correction module 460 may be implemented in hardware, software, or a combination thereof. Also, the landmark correction module 460 may be separate for or provided as part of the processor 408.

The processed signals representative of the image are also transmitted to the display device 448 to provide a visual display of the image. Specifically, the MR signals fill or form a k-space that is Fourier transformed to obtain a viewable image. The processed signals representative of the image are then transmitted to the display device 448.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as an optical disk drive, solid state disk drive (e.g., flash RAM), and the like. The storage device may also be other similar means for loading computer programs or other instructions into the computer or processor.

As used herein, the term "computer" or "module" may include any processor-based or microprocessor-based system including systems using microcontrollers, Reduced Instruction Set Computers (RISC), Application Specific Integrated Circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from the scope thereof. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. A non-transitory computer readable storage medium for landmark correction in Magnetic Resonance Imaging (MRI) using a processor, the non-transitory computer readable storage medium including instructions to command the processor to:
    acquire at least one calibration image or at least one localizer image of an object;
    identify in the calibration or localizer images a region of the object as a reference point, the reference point defining a landmark position;
    determine an offset between an initial landmark position and the identified landmark position; and
    use the determined offset for MRI;
    wherein the at least one localizer image comprises a plurality of two-plane image slices and the instructions command the processor to identify a torso outline of the object using an axial image of the plurality of two-plane images.

2. The non-transitory computer readable storage medium of claim 1, wherein the instructions command the processor to apply an offset correction for image reconstruction using the determined offset.

3. The non-transitory computer readable storage medium of claim 1, wherein to use the determined offset for MRI, the instructions command the processor to generate a notification to a user of the determined offset to allow a user to move the object based on the notification.

4. The non-transitory computer readable storage medium of claim 1, wherein to use the determined offset for MRI, the instructions command the processor to automatically move the object based on the determined offset.

5. The non-transitory computer readable storage medium of claim 1, wherein the initial landmark position is from a manual landmarking process.

6. The non-transitory computer readable storage medium of claim 1, wherein the initial landmark position is from an automatic landmarking process.

7. The non-transitory computer readable storage medium of claim 1, wherein the initial landmark position is from a fixed landmarking process.

8. The non-transitory computer readable storage medium of claim 1, wherein to use the determined offset for MRI, the instructions command the processor to notify an operator to manually move the object based on the determined offset.

9. The non-transitory computer readable storage medium of claim 1, wherein the instructions command the processor to identify lungs of the object from the at least one calibration image.

10. The non-transitory computer readable storage medium of claim 9, wherein the instructions command the processor to determine a superior/inferior (S/I) difference between the identified lungs and reference lungs and use the determined S/I difference as the determined offset.

11. The non-transitory computer readable storage medium of claim 1, wherein the instructions command the processor to determine the offset based on a comparison of the identified torso with a reference image to form a torso centered coronal image.

12. The non-transitory computer readable storage medium of claim 11, wherein the instructions command the processor to localize and segment lungs on the torso centered coronal image and determine a superior/inferior (S/I) difference between the localized and segmented lungs and reference lungs and use the determined S/I difference as the determined offset.

13. The non-transitory computer readable storage medium of claim 1, wherein the at least one localizer image comprises a plurality of three-plane image slices and the instructions command the processor to determine a center of a head of the object in left-right and anterior-posterior directions using an axial image of the plurality of three-plane image slices and determine a superior most location of the head using sagittal and coronal images of the plurality of three-plane image slices.

14. The non-transitory computer readable storage medium of claim 13, wherein the instructions command the processor to determine a new landmark based on the determined superior most location of the head.

15. The non-transitory computer readable storage medium of claim 1, wherein the at least one localizer image comprises a single axial image slice acquired at an iso-center of an MRI magnet and a single sagittal image slice, and wherein the instructions command the processor to determine a center of a knee of the object in left-right and anterior-posterior directions using the single axial image slice and determine a joint location of the knee of the object using the single sagittal image slice.

16. The non-transitory computer readable storage medium of claim 15, wherein the instructions command the processor to determine a new landmark based on the determined joint location.

17. The non-transitory computer readable storage medium of claim 1, wherein the landmark position is an anatomical landmark position and the instructions command the processor to determine a distance from the anatomical landmark position to an iso-center of an MRI magnet.

18. The non-transitory computer readable storage medium of claim 17, wherein the instructions command the processor to at least one of (1) notify an operator to reposition the patient, (2) notify the operator to increase a field or view for the MRI or (3) automatically increase the field of view for the MRI, if the distance exceeds a threshold.

19. A Magnetic Resonance Imaging (MRI) system comprising:
- an imaging portion configured to acquire MRI images including at least one calibration image or localizer image of an object; and
- a processing portion having a landmark correction module configured to identify in the calibration or localizer images a region of the object as a reference point, the reference point defining a landmark position, determine an offset between an initial landmark position and the identified landmark position, and use the determined offset for MRI imaging by the imaging portion;
- wherein the landmark correction module is further configured to at least one of (1) notify an operator to reposition the patient, (2) notify the operator to increase a field or view for the MRI or (3) automatically increase the field of view for the MRI, if a determined distance from the identified landmark position to an iso-center of an MRI magnet exceeds a threshold.

20. The MRI system of claim 19, wherein the landmark correction module is further configured to apply an offset correction for image reconstruction using the determined offset.

21. The MRI system of claim 19, wherein the landmark correction module is further configured to use the determined offset for MRI to generate a notification to a user of the determined offset to allow a user to move the object based on the notification.

22. The MRI system of claim 19, wherein the landmark correction module is further configured to use the determined offset for MRI to automatically move the object based on the determined offset.

23. The MRI system of claim 19, wherein the initial landmark position is from a manual landmarking process.

24. The MRI system of claim 19, wherein the initial landmark position is from an automatic landmarking process.

25. The MRI system of claim 19, wherein the initial landmark position is from a fixed landmarking process.

26. The MRI system of claim 19, wherein the landmark correction module is further configured to use the determined offset for MRI to notify the operator as to manually move the object based on the determined offset.

27. A method for landmark correction in Magnetic Resonance Imaging (MRI) using the MRI system of claim 19, the method comprising:
- acquiring at least one calibration image or at least one localizer image of an object;
- identify in the calibration or localizer images a region of the object as a reference point, the reference point defining a landmark position;
- determining an offset between an initial landmark position and the identified landmark position; and
- using the determined offset for MRI.

* * * * *